United States Patent [19]

Carrington

[11] 4,011,270
[45] Mar. 8, 1977

[54] RECRYSTALLIZED MENTHOL PRODUCT AND METHOD OF MAKING

[75] Inventor: Richard Gardner Carrington, Chehalis, Wash.

[73] Assignee: I. P. Callison & Sons, Inc., Seattle, Wash.

[22] Filed: May 28, 1974

[21] Appl. No.: 473,733

[52] U.S. Cl. .................. 260/631 R; 23/295 R; 131/17 R; 260/707; 426/538; 426/590

[51] Int. Cl.² .................................. C07C 35/12

[58] Field of Search .............. 260/631 R; 23/295 S

[56] References Cited

OTHER PUBLICATIONS

The Merck Index, p. 653, 8th Ed., Merck & Co., (1968).
Bliss et al., The Journal of the American Pharmaceutical Association, vol. XXIX, pp. 171–175, 1940.

Wright, "J. Am. Chem. Soc.," vol. 39, pp. 1515–1524, (1917).

Primary Examiner—Donald G. Daus
Assistant Examiner—David B. Springer
Attorney, Agent, or Firm—Seed, Berry, Vernon & Baynham

[57] ABSTRACT

A recrystallized menthol product derived from crude natural menthol is described for incorporation into foods, beverages and tobacco in amounts sufficient to create a lingering cool sensation in the mouth of the user of the food, beverage or tobacco with little or no taste of menthol. The recrystallized menthol product is recrystallized from an ethanol-water solution of crude natural menthol under specific conditions.

6 Claims, No Drawings

RECRYSTALLIZED MENTHOL PRODUCT AND METHOD OF MAKING

BACKGROUND OF THE INVENTION

1. Field of the Invention

This invention relates to a method of obtaining a menthol product by recrystallization from crude natural menthol, to the recrystallized menthol produce per se and the use of the recrystallied menthol produce in foods, beverages or tobacco.

2. Prior Art Relating to the Disclosure

Menthol has long been used for a flavorant in foods, beverages and tobacco. Menthol is obtained from both synthetic and natural sources. The menthol obtained from natural sources is generally purified by freeze recrystallization from solutions of the crude product. It has been thought that the larger the crystals obtained, the more pure the menthol obtained. It is known that there are eight possible isomers of menthol, six of which exist in nature. Two sets of four isomers of menthol have equal and opposite optical rotation. The natural menthol, generally imported from Brazil, Taiwan or Japan, when incorporated in beverages, foods or tobacco, gives a cooling sensation in the mouth of the user of the product incorporating the menthol; however, the cooling effect carries with it the medicinal taste of menthol.

SUMMARY OF THE INVENTION

It is a primary object of this invention to provide a menthol product recrystallized from natural menthol crystals which, when incorporated in foods, beverages and tobacco, creates a lingering cool sensation in the mouth of the user of the food, beverage or tobacco with little or no detection of the menthol taste. The recrystallized menthol product differs in its properties from natural menthol in (1) organoleptic qualities (odor and taste), (2) density of the crystalline mass, (3) crystal structure, size and shape, (4) solubility, and (5) gravity filtration rate.

It is a further object of this invention to provide a method for obtaining a menthol product having the previously described properties by dissolving natural menthol crystals in an alcohol-water solution, allowing phase separation and recrystallizing the menthol product from the phase containing liquid menthol.

It is a further object of this invention to provide a method of obtaining a menthol product having the previously described properties wherein recrystallization is carried out by suspending a glass rod or synthetic plastic-coated rod in the phase of the alcohol-water solution containing the liquid menthol, with the lower end of the rod at the interface between the two phases.

It is a further object of this invention to provide a menthol product creating a lingering cooling sensation in the mouth of the user with little or no accompanying menthol taste.

DESCRIPTION OF THE PREFERRED EMBODIMENTS

Crude natural menthol crystals, such as Brazilian Arvensis menthol crystals or menthol crystals from other sources, such as Japan and Taiwan, are pulverized and dissolved in an alcohol-water solution. The alcohol used is preferably ethanol. The ratio of alcohol to water may vary from 20–40% by volume alcohol, but preferably about 25% by volume alcohol and 75% water.

The amount of menthol dissolved in the alcohol-water solution is not particularly critical and may range from a weight ratio of menthol to alcohol-water solution of from 1:1 to 1:5. Some degree of warming may be necessary to effect dissolution of the natural menthol crystals in the alcohol-water solution. The menthol is dissolved with agitation and gives a milky appearing emulsion which is allowed to stand, preferably at ambient temperature (18°–25° C.), until phase separation occurs. Two phases form: an upper phase, which is clear and water-like and which contains liquid menthol and alcohol, and a lower phase, milky in appearance and containing primarily water along with alcohol, small amounts of dissolved menthol and residual impurities.

The menthol product which is the subject of this invention is recrystallized from the upper phase, preferably by suspending a rod in the upper phase with the lower end of the rod touching the interface between the upper and lower phases but not entering the lower phase. Recrystallization is best carried out in a clear glass vessel using a glass rod or rod of other material coated with synthetic resin, such as polyethylene or polypropylene. The temperature at which recrystallization is carried out appears to be a determining factor in the type and quantity of crystals obtained. The recrystallization temperature is preferably around ambient, i.e., 18°–25° C., preferably about 22° C.

After suspension of the rod in the upper phase of the alcohol-water solution, crystallization begins and is evident in two different places: (1) on the side wall of the container above the liquid level, generally on the side of the container or vessel subjected to sunlight, and (2) simultaneously on the suspended rod above the liquid level. The majority of the crystallization occurs on the rod and the crystals do not contact any portion of the liquid in most instances. The time necessary for complete crystallization varies but is generally around 24 hours. After about 8–12 hours, the crystals formed on the rod and side walls of the vessel are generally removed to allow formation of additional crystals. During crystallization, there appears to be a very marked phototropic effect as crystallization occurs on the side walls of the container subjected to sunlight. When the container is turned, the site of crystallization changes to orient itself to the direction of the sunlight.

The menthol crystals recovered by the recrystallization process differ markedly from the starting natural menthol crystals. The crystal structure of the recrystallized product is vastly different in shape, type and size from the original raw material. The starting crystals are generally large, needle-like crystals, whereas the crystals obtained by the process outlined above are less than 1/32 inch in diameter and almost amorphous in nature. The organoleptic qualities of the recrystallized menthol product are readily distinguishable from the starting menthol crystals in both odor and taste. The solubility of the recrystallized menthol crystals differs from that of the starting menthol crystals in that they are more difficult to solubilize. The density of the recrystallized menthol is less than the density of the starting crystals. The recrystallized product described floats in a refined coconut oil solvent while the starting crystals sink. It was also noted that when re-solution was attempted, a considerable difference in gravity filtration rate was observed in the recrystallized menthol compared to the gravity filtration rate of the starting menthol crystals using identical solvent systems, each containing the same concentration of menthol. It is not known to what the attribute the difference in properties in the product obtained by recrystallization and those of the starting menthol crystals. The recrystallized product may be a pure form of menthol or contain a different ratio of menthol isomers.

It was found that when the recrystallized menthol product was incorporated in beverages, such as tea, chocolate, soft drinks, etc., in relatively small amounts, it created a lingering cool sensation in the mouth of the user lasting as long as 20-30 minutes with little or no taste of menthol. The recrystallized product can be used at such a minimal level that the menthol taste cannot be detected and yet still achieve the lingering cool sensation.

The following examples are illustrative of the invention but are not intended to be limiting in any way.

EXAMPLE I 200 units by weight of crude, natural, Brazilian Arvensis menthol crystals were dissolved in a clear glass beaker containing 500 units by weight of an ethyl alchol-water solution containing 25% by volume of 95% SDA N0. 3A ethyl alcohol in distilled water. The solution was warmed slightly, with agitation, to thoroughly dissolve and mix the crystals to form a fast-breaking, milky appearing emulsion.

The solution was allowed to stand at ambient temperature (about 22° C.) until separation of the phases occurred. The upper phase was crystal clear and contained liquid menthol and alcohol. The lower phase was milky in appearance and contained primarily water with some alcohol and small amounts of dissolved menthol and residual impurities.

A polypropylene-coated steel rod was vertically suspended in the upper phase. The rod was lowered into the upper phase until its lower end touched the interface between the upper and lower phases. In less than 1 hour, crystallization began and was evident in two places: (1) on the side wall of the glass beaker above the liquid level and on the side of the beaker subjected to natural sunlight, and (2) on the polypropylene-coated rod above the liquid level. The majority of the crystallization occurred on the rod. No crystals were in contact with any portion of the liquid, in most instances.

The crystal structure of the recrystallized menthol product was vastly different in shape, type and size from the original starting material, and its organoleptic qualities, i.e., odor and taste, were readily distinguishable from the starting natural menthol crystals.

EXAMPLE II

Recrystallization was attempted as in Example I using, however, synthetic menthol crystals. It was found that the use of any portion of synthetic crystals retarded or completely prevented recrystallization.

It was also found that rapid or moderately rapid lowering of temperature during recrystallization prevented recrystallization into the crystalline menthol product described.

Recrystallization was attempted in a stainless steel vessel. Very little recrystallization was obtained and the recrystallized menthol was of poor quality.

The alcohol-water solvent of Example I was used for a second recrystallization. A recrystallized product was obtained but was not the same in terms of odor and taste as that obtained by the first recrystallization.

The menthol product of the first recrystallization was subjected to a second recrystallization to see if further refinement would produce a still more desirable product. This was not the case.

For reasons not understood, the desired cooling sensation obtained with the recrystallized menthol product is not as definite if any portion of the crystals is recovered from the liquid phase.

Two samples were made up for comparison on sensitive chromatographic equipment. One sample contained 30% by volume of crude, natural, Brazilian Arvensis menthol crystals dissolved in a refined coconut oil. A second sample contained 30% by volume of the menthol crystals described herein recrystallized from the Arvensis menthol crystals and dissolved in the same refined coconut oil. Both solutions were run on a gas chromatograph. The results indicated that both solutions contained two minor contaminants which eluted immediately ahead of the main menthol peak using a Silar 10C column for analysis. The concentration of these minor contaminants was less than 0.1% of the menthol content of the samples. A significant variation in the menthol content of the two samples was observed, however. In fact, the two samples contained the same amount of menthol and it is believed that the difference in menthol content detected by the gas chromatographic analysis is indicative of a change in the isomeric relationship of the various isomers of menthol. It is believed that the recrystallization process not only results in a clean product but also results in an isomeric rearrangement of menthol isomers which gives a relative ratio of isomers of uniqueness which results in the cool, clean taste sensation and the lingering cool sensation.

The recrystallized menthol product dissolved in refined coconut oil solvent may be applied to tobacco by spray deposition or other suitable process or incorporated into foodstuffs, such as candy. For incorporation in beverages, such as, for example, carbonated beverages, the menthol dissolved in the coconut oil solvent is placed in an emulsion, such as water-sorbitol-dispensing agent emulsion, and relatively small amounts of the emulsion (0.1 cc. emulsion in 10 oz. beverage, the emulsion containing about 6% menthol product) incorporated into the beverage. The recrystallized menthol product of this invention has a particular advantage when incorporated into artificially sweetened beverages in that the cool, clean taste covers the aftertaste generally associated with artificial sweeteners.

The embodiments of the invention in which a particular property or privilege is claimed are defined as follows:

1. A method of obtaining a menthol product from crude natural menthol, comprising the steps of:
    dissolving the crude natural menthol in an alcohol-water solution containing 20–40% by volume ethyl alcohol, with the remainder water, to form an emulsion thereof at a temperature ranging from 18°–25° C.,
    allowing phase separation of the emulsion in a clear glass vessel into an upper phase and a lower phase, the upper phase containing liquid menthol and ethyl alcohol and the lower phase containing primarily water, some alcohol and residual liquid menthol, and in the presence of light suspending a glass rod or synthetic plastic-coated glass rod in the upper phase with the lower end of the rod touching the interface between the upper and lower phases but not entering the lower phase, the menthol contained in the upper phase recrystallizing on the rod above the liquid level of the upper phase.

2. The method of claim 1 wherein 150–300 parts of crude natural menthol crystals are dissolved in 500 parts of the alcohol-water solution.

3. The method of claim 1 wherein the rod is coated with a solid, synthetic resin selected from the group consisting of polyethylene and polypropylene.

4. The method of claim 1 wherein recrystallization is carried out in the presence of sunlight.

5. A method of obtaining a menthol product comprising the steps of:
dissolving, with agitation, in a clear glass vessel crude natural menthol crystals in an ethyl alcohol-water solution to form an emulsion thereof, the alcohol-water solution containing from 20–40% by volume ethyl alcohol,
allowing the emulsion to stand at ambient temperature in the presence of sunlight until phase separation into an upper phase and a lower phase occurs, the upper phase being crystal clear in appearance and containing liquid menthol and alcohol and the lower phase being milky in appearance and containing primarily water, some alcohol and small amounts of dissolved menthol,
vertically suspending a rod having an outer exposed surface of a solid synthetic resin selected from the group consisting of polyethylene and polypropylene in the upper phase with the lower end of the rod touching the interface between the upper and lower phases but not entering the lower phase,
allowing crystallization to occur at ambient temperature, crystallization occurring on the side walls of the clear glass vessel above the level of the liquid in the vessel and the side wall of the container subjected to sunlight with the majority of the crystallization occurring on the rod above the level of the upper phase in the container, and
recovering the recrystallized product from the side walls of the vessel and the rod without contact with any portion of the upper liquid phase.

6. A crystalline menthol product obtained from crude menthol crystals by:
dissolving crude natural menthol in an alcohol-water solution containing 20–40% by volume ethyl alcohol and the remainder water in a glass vessel at a temperature ranging from 18°–25° C. to form an emulsion thereof,
allowing phase separation of the emulsion in a clear glass vessel into upper and lower phases, the upper phase being clear and containing liquid menthol and alcohol and the lower phase being milky in appearance and containing primarily water, along with some alcohol and residual liquid menthol, and in the presence of light
suspending a glass rod or a synthetic plastic-coated glass rod in the upper phase with the lower end of the rod touching the interface between the upper and lower phases but not entering the lower phase, the crystalline menthol product recrystallizing on the rod above the liquid level of the upper phase, the rod having an outer exposed surface of a material selected from the group consisting of glass, polyethylene or polypropylene.

* * * * *